(12) United States Patent
Qazi et al.

(10) Patent No.: US 6,686,375 B2
(45) Date of Patent: Feb. 3, 2004

(54) **COMPOSITION USEFUL AS HEPATOPROTECTANTS COMPRISING EXTRACT OF PLANT *CRYPTOLEPIS BUCHANANI* AND A METHOD THEREOF**

(75) Inventors: Ghulam Nabi Qazi, Jammu (IN); Bupinder Singh Jaggi, Jammu (IN); Bal Krishan Chandan, Jammu (IN); Krishnan Avtar Suri, Jammu (IN); Naresh Kumar Satti, Jammu (IN); Rakesh Maurya, Jammu (IN); Lila Ram Manhas, Jammu (IN); Ashwani Kumar, Jammu (IN); Bal Krishnan Kapahi, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/107,671

(22) Filed: Mar. 26, 2002

(65) Prior Publication Data

US 2003/0185906 A1 Oct. 2, 2003

(51) Int. Cl.[7] ........................ A61K 35/78; A01N 65/00; A01N 27/00; A01N 25/00

(52) U.S. Cl. ....................... 514/310; 514/783; 514/893; 514/894; 514/885; 424/725; 424/773; 424/774; 424/779

(58) Field of Search ................ 514/310, 783, 514/893, 894, 885; 424/725, 773, 779, 774

(56) References Cited

U.S. PATENT DOCUMENTS 6,548,086 B1 * 4/2003 Maurya et al. ............. 424/725

\* cited by examiner

*Primary Examiner*—Frederick Krass
*Assistant Examiner*—Clinton Ostrup
(74) *Attorney, Agent, or Firm*—Morgan & Finnegan LLP

(57) ABSTRACT

The present invention relates to a composition useful for hepatoprotection, said composition comprising polar extract of plant *Cryptolepis Buchanani* and/or fractions of the said extract, and optionally pharmaceutically acceptable additives and a method of producing said composition and also a method of treating a subject using said composition.

13 Claims, No Drawings

COMPOSITION USEFUL AS HEPATOPROTECTANTS COMPRISING EXTRACT OF PLANT CRYPTOLEPIS BUCHANANI AND A METHOD THEREOF

FIELD OF INVENTION

The present invention relates to a composition useful for hepatoprotection, said composition comprising polar extract of plant *Cryptolepis Buchanani* and/or fractions of the said extract, and optionally pharmaceutically acceptable additives and a method of producing said composition and also a method of treating a subject using said composition.

BACKGROUND AND PRIOR ART REFERENCES

*Cryptolepis buchanani* Roem. & Schult. (Family Asclepiadaceae) is distributed throughout hot deciduous forests of India and holds a very prestigious position in Ayurveda.

It is a very useful plant because of its multiple uses as a traditional medicine, such as anti-diarrheal, anti-bacterial, anti-ulcerative, anti-inflammatory, blood purifier and for lactation in women [Bhakuni, D. S., Dhar, M. L., Dhar, M. M., Dhawan, B. N., and Mehrotra, B. N.,. *Ind. J. Expt. Biol.,* 7: 250–262 (1969), Bhav Prakash, Commentary on Bhav Prakash Nighantu edited by C. K. Chunekar, Chowkhamba Vidya Bhavan, Varanasi $4^{th}$ edition: 427 (1969)].

Ethanolic extract of roots and stem show hypotensive, central nervous system depressant and antiamphetaminic activity [Joshi, M. C., Patel, M. B. and Mehta, P. *J. Bull. Med. Ethno. Bot. Res.,* 1: 8–24 (1980)].

Ethanolic extract of aerial parts of plant shows diuretic activity [Dhawan, B. N., Patnaik, G. K., Rastogi, R. P., Singh, K. K. and Tandon, J. S., *Ind. J. Expt. Biol.,*15: 208–219 (1977)].

Root bark is used in rheumatic pains [Mudgal, V. and Pal, D. C., Bull. *Bot. Surv. Ind.,* 22: 59–62 (1980)].

Stem constituents are alkaloids and triterpenes, leaves constituents are α and β amyrin ( Asolkar, L. V., Kakkar, K. K. and Chakre, O. J., Glossary of Indian Medicinal Plants with active principles, part-1, A-K., 1965–1981(1992)] and cryptolepine—the methyl-quinolanol alkaloid of *cryptolepis sanguinolenta*. Pyridine alkaloid, buchanine [Dutta, Sunil K, Sharma, Batuk N, Sharma, Priya V. *Phytochemistry* 17, 2047(1978)] and a cardenolide cryptosin, 7,8-Epoxy-3,11, 14-trihydroxy-12-Oxocard 20 (22)-enolide [Venkateshwara R; Narendra N; Viswametra M. A; Vaidyanathan C. S.; *Phytochemistry* 28, 1203 (1989)] are the major chemical constituent of the plant. Apart from these chemical constituents cryptanoside —A to D and germenicol [Purshothman K. K; Saradha V; Connolly J. D; Rycroft D. S, *Rev. Latinomer Quim.,* 19, 28 (1988)], 1,3,6-trinicotinoyl-β-D-glucopyranoside and 1,3,6-trinicotinoyl-α-D-glucopyranoside, n -trinicontanol, n-triactonoic acid, β-amyrin and β-sitosterol glucoside [Dutta S. K; Sharma B. N; Sharma P. V., *Phytochemistry,* 17, 2047 (1978), Dutta S. K; Sharma B. N, Sharma P. V; (1980) *Phytochemistry,* 19, 1278 (1980)].

The alcoholic extract of the root shows the presence of sterols, reducing sugars and traces of glycosides and exhibited antiplatelet effects in vitro in humans, rabbits and rats. In rats, it exhibited ADP-aggregation in vitro with delayed onset and prolonged action. It exhibited an indirect fibrinolytic action in the rat possibly by causing the release of plasminogen activators from the vascular endothelium [Oyekan, A. O., Botting, J. H. and Noamesi, B. K., General Pharmacol., 19: 223–227 (1988)].

Liver has a pivotal role in regulation of physiological processes. Toxic chemicals and infections mainly cause liver diseases. Hepatocyte alterations of various origins result in acute and chronic dysfunctions, which may be lethal [Decker K. and Keppler D. Rev. *Physiol. Biochem. Pharmacol.,* 71, 79–106 (1974)].

Liver disorders are still the major hazard both in urban and rural population. Despite scientific advances in our understanding in the management of liver disorders and the leads provided by traditional system of medicine, no specific treatment for liver ailments is available except a few herbal preparations, WHO, Regional Office Manila, 1993.; [Subeamoniam and Pushpangadan, *Indian Journal of Pharmacology,* 31,166–175 (1999)].

It is emphasized that hepatotoxin that causes acute hepatitis should have close resemblance with the viral hepatitis, clinically, biochemically and histologically. In many instances drug induced hepatitis proves indistinguishable from viral hepatitis. Chemically induced hepatic injury for experimental studies should be severe enough to cause death or to modify hepatic function. The mechanism of acute hepatic injury depends upon the chemical compound and the species of animals used. Many chemicals produce parenchymal damage (cytotoxic injury), arrest bile flow and cause jaundice. The damage may be acquired or toxicological phenonmenon, therapeutic misadventure or induced experimentally. Drugs also cause chronic hepatic diseases such as hepatitis, fatty liver, cirrhosis, and several vascular lesions of the liver.

It is the role of hepatoprotective agents to interfere with these pathological processes by blocking their evolution and helping recovery by preventing hepatocytes degeneration, necrosis, steatosis and inflammation, stimulate regeneration processes, and inhibit fibrosis which leads to cirrhosis and death [Doreswamy, R., Sharma, D., *Indian Drugs,* 32, 139–144 (1995)], Kumar et al, Cell injury and adaptation. In: "Basic Pathology", $5^{th}$ Edn. Prime Books (pvt.) Ltd., Banglore, India. 1992, pp. 3–24.

Acute hepatitis closely resembling viral hepatitis clinically, biochemically and histologically, can be produced by chemicals and drugs in humans and experimental animals, [AL-Tuwaijiri A. et al Heptology, 51: 107–113 (1981); Decker K. and Keppler D. *Rev Physiol. Biochem. Pharmacol.,* 71, 79–106 (1974); Kumar et al, Cell injury and adaptation. In: "Basic Pathology", $5_{th}$ Edn. Prime Books (Pvt.) Ltd., Banglore, India. 1992, pp. 3–24].

OBJECT OF THE PRESENT INVENTION

The main object of the present invention is to develop a composition comprising extract from plant *Cryptolepis buchanani* and/or its fractions.

Another main object of the present invention is to develop a composition comprising plant *Cryptolepis buchanani* having hepatoprotective activity.

Yet another object of the present invention is to develop a method of producing a composition comprising extract from plant *Cryptolepis buchanani* and/or its fractions having hepatoprotection activity.

Still another object of the present invention is to develop a method of treating a subject including animals and/or humans for hepatoprotection, using a composition comprising extract from plant *Cryptolepis buchanani* and/or its fractions. Still another object of the present invention is to develop a composition extract from plant *Cryptolepis buchanani* and/or its fractions with better hepatoprotective activity as compared to commercially available hepatoprotective drugs.

SUMMARY OF THE PRESENT INVENTION

The present invention relates to a composition useful for hepatoprotection, said composition comprising polar extract of plant *Cryptolepis Buchanani* and/or fractions of the said extract, and optionally pharmaceutically acceptable additives and a method of producing said composition and also a method of treating a subject using said composition.

DETAILED DESCRIPTION OF THE PRESENT INVENTION

Accordingly, the present invention relates to a composition useful for hepatoprotection, said composition comprising polar extract of plant *Cryptolepis Buchanani* and/or fractions of the said extract, and optionally pharmaceutically acceptable additives and a method of producing said composition and also a method of treating a subject using said composition.

In an embodiment of the present invention, a composition useful for hepatoprotection, said composition comprising effective amount of polar solvent extract (A001) from plant *Cryptolepis buchanani* and optionally pharmaceutically acceptable additives.

In another embodiment of the present invention, wherein said additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In yet another embodiment of the present invention, wherein polar solvents are selected from a group comprising alcohol, rectified spirit, aqueous rectified spirit, and water.

In still another embodiment of the present invention, wherein said extract and additives are in the ratio ranging between 1:1 to 1:10.

In a further embodiment of the present invention, wherein a method of preparing polar solvent extract A001 and its four fractions F001, F002, F003, and F004 from plant *Cryptolepis buchanani* having hepatoprotective activity.

In another embodiment of the present invention, powdering said plant.

In yet another embodiment of the present invention, percolating said powder in cold with polar solvent.

In still another embodiment of the present invention, concentrating said percolate to prepare polar solvent extract (A001).

In still another embodiment of the present invention, triturating said extract successively with solvents of increasing polarity using hexane and chloroform.

In still another embodiment of the present invention, collecting fractions F001 and F002 respectively with said solvents and a residue.

In still another embodiment of the present invention, portioning said residue between n-butanol and water of ratio 5:1.

In still another embodiment of the present invention, collecting n-butanol soluble fraction (F003) and water soluble fraction (F004).

In still another embodiment of the present invention, wherein root and aerial part of said plant are preferred plant parts for said activity.

In still another embodiment of the present invention, wherein polar solvent is selected from a group comprising methanol, propanol, and ethanol.

In still another embodiment of the present invention, wherein polar solvent is preferably 95% ethanol.

In still another embodiment of the present invention, wherein percolated plant in polar solvent is at concentration ranging between 100–500 gms/liter.

In still another embodiment of the present invention, wherein percolation is for time duration ranging between 14–18 hours.

In still another embodiment of the present invention, wherein percolated extract is concentrated by evaporation under reduced pressure.

In still another embodiment of the present invention, wherein percolated extract is concentrated at temperature ranging between 40–50° C.

In still another embodiment of the present invention, wherein percolated extract is concentrated at temperature preferably about 45° C.

In still another embodiment of the present invention, wherein percolated extract is finally dried in vacuum.

In still another embodiment of the present invention, wherein trituration rate is ranging between 15–35 ml/minute.

In still another embodiment of the present invention, wherein trituration rate is preferably about 23 ml/minute.

In still another embodiment of the present invention, wherein triturating with each of the said solvents for time duration ranging between 20 to 40 minutes.

In still another embodiment of the present invention, wherein said fractions have concentration of F001—about 11% (w/w), F002—about 15% (w/w), F003—about 40% (w/w), and F004—about 35% (w/w).

In a further embodiment of the present invention, a composition useful for hepatoprotection, said composition comprising effective amount of fraction F003 of claim 5 from plant *Cryptolepis buchanani*, and optionally pharmaceutically acceptable additives.

In still another embodiment of the present invention, wherein additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In still another embodiment of the present invention, wherein said fraction and additives are in a ratio ranging between 1:1 to 1:10.

In yet another embodiment of the present invention, a method of treating subjects for developing hepatoprotection using composition comprising effective amount of extract A001 and/or fraction F003 from plant *Cryptolepis buchanani* and optionally pharmaceutically acceptable additives.

In still another embodiment of the present invention, wherein the additive is selected from a group of nutrients comprising proteins, carbohydrates, sugar, talc, magnesium stearate, cellulose, calcium carbonate, starch-gelatin paste, and/or pharmaceutically acceptable carrier, excipient, diluent or solvent.

In still another embodiment of the present invention, wherein said composition is effective against hepatotoxins selected from a group comprising Paracetamol, D-Galactosamine, and Carbon tetrachloride.

In still another embodiment of the present invention, wherein said method involves administering said extract and/or fraction orally, inhaled, or implanted.

In still another embodiment of the present invention, wherein the physical state of said composition for the oral route is in the form of capsule, tablet, syrup, concentrate, powder, granule, aerosol, or beads.

In still another embodiment of the present invention, wherein said extract and fraction are in a ratio ranging between 1:10 to 10:1.

In still another embodiment of the present invention, wherein administering said extract and/or fraction at concentration ranging between 100–500-mg/kg. In still another embodiment of the present invention, wherein administering said extract and/or fraction at concentration preferably about 270 mg/kg.

In still another embodiment of the present invention, wherein said composition of said extract and optionally pharmaceutically acceptable additives shows % hepatoprotective activity of GPT ranging between 70–90, GOT ranging between 65–95, ALP ranging between 70–95, Bilirubin ranging between 65–95, Triglycerides ranging between 60–99, Lipid Peroxidation ranging between 70–95, and Glutathione ranging between 65–99.

In still another embodiment of the present invention, wherein said composition of said fraction and optionally pharmaceutically acceptable additives shows % hepatoprotective activity. of GPT ranging between 60–80, GOT ranging between 55–65, ALP ranging between 65–75, Bilirubin ranging between 70–80, Triglycerides ranging between 60–65, Lipid Peroxidation ranging between 65–85, and Glutathione ranging between 65–85.

In still another embodiment of the present invention, said method is useful for treating animals and/or human beings.

In still another embodiment of the present invention, wherein said method shows said composition to be more effective than commercially available hepatoprotectants.

In still another embodiment of the present invention, wherein said method using said composition has no adverse effect on health.

This invention relates to hepatoprotective activity of an extract and fraction from *Cryptolepis buchanani*.

In an embodiment of the present invention, invention relates to hepatoprotective activity of an extract and fraction from *Cryptolepis buchanani*, isolated from the fraction by extracting powdered roots, aerial part, whole plant, in a polar solvent like rectified spirit, methanol, aqueous rectified spirit, water in glass percolator, removing fatty non-polar constituents by triturating with hexane, dichloromethane, chloroform or ethyl acetate, to get fraction, suspended in water, partitioned with n-butanol to furnish active fraction.

In yet another embodiment of the present invention is described a extract, and fraction possessing hepatoprotective activity.

In still another embodiment of the present invention; the plant material is powdered by conventional methods.

In still another embodiment of the present invention, the alcoholic extract of the plant material is prepared by cold percolation using propanol, methanol, ethanol, or n-butanol.

In still another embodiment of the present invention, the alcoholic extract (A001) is concentrated by conventional method.

In still another embodiment of the present invention, successive trituration i.e., shaking the extract with the solvent] is done using the alcoholic extract with hexane, and chloroform to get hexane soluble fraction (F001) and chloroform soluble fraction (F002) and residue.

In still another embodiment of the present invention, residue obtained as above is suspended in water.

In still another embodiment of the present invention, the fraction is then extracted with n-butanol, to furnish n-butanol soluble fraction (F003), In still another embodiment of the present invention, hepatoprotective activity of extract and fraction is calculated.

In still another embodiment of the present invention, Applicants product is more potent than the commercially available herbal hepatoprotective agents.

In still another embodiment of the present invention, the said compounds are compared with latest hepatoprotective drug SILYMARIN marketed by M/S Ranbaxy (INDIA) LTD.

In still another embodiment of the present invention, significant information is obtained on the hepatoprotective activity of the said compounds in experimental animals against Paracetemol, Galactosamine and CCL4 as Hepatoxins.

BRIEF DESCRIPTION OF ACCOMPANYING DRAWING

FIG. 1 shows Flow Sheet Chart of extraction and fractionation process of plant *cryptolepis buchanani*.

The invention is described in detail by the examples given below which should not be construed to the limit of scope of the present invention.

EXAMPLE 1

The shade dried, powdered *Cryptolepis buchanani* roots (2.7 kg) were extracted with rectified spirit by cold percolation (5×16 hours). The rectified spirit was evaporated under reduced pressure to obtain a brown mass (215 g, A001); this was submitted for hepatoprotective activity, further this extract was triturated successively with hexane, chloroform, to furnish hexane soluble fraction (23.0 g, F001) and chloroform soluble fraction (28.0 g F002). The residue left was dissolved in water, and extracted with n-butanol, the n-butanol soluble fraction (80.0 g, F003), these extract and fractions were subjected for activity testing and fraction F003 was subjected for the isolation of compounds by column chromatography over silica gel (230 400 mesh), column was eluted with mixture of chloroform-methanol (19:1), furnished 1 (30 mg) and 2 (50 mg). (Please refer Table 1 at the end after claims)

TABLE 1

Hepatoprotective activity (in vivo) of RJM/0024/P01/A001, RJM/0024/P01/A001/F001, RJM/0024/P01/A001/F002, RJM/0024/P01/A001/F003, RJM/0024/P01/A001/F004 and silymarin (Pre-treatment fed at 72 h, 48 h, 24 h, 1 h) before inhalation of diethyl-ether and 1 h after Acetaminophen [(APAP) 200 mg kg$^{-1}$ i.p.) given 6 h after exposure to diethyl-ether in mice$^a$ % Hepatoprotection

| Treatment | Dose Mg/kg (p.o.) | Serum parameters | | | Hepatic parameters | |
|---|---|---|---|---|---|---|
| | | GPT (Units) | GOT (Units) | ALP$^b$ | Lipid peroxidation$^c$ | Glutathione$^d$ |
| AOO1 + APAP | 250 | 84.02 | 85.08 | 91.33 | 89.10 | 95.11 |
| F001 + APAP | 250 | 30.40 | 48.62 | 30.64 | 54.35 | 49.65 |
| F002 + APAP | 250 | 40.99 | 52.63 | 35.03 | 50.81 | 58.42 |
| F003 + APAP | 250 | 60.00 | 61.79 | 70.82 | 78.72 | 80.75 |
| F004 + APAP | 250 | 47.52 | 50.34 | 50.01 | 53.37 | 63.23 |
| Silymarin + APAP | 50 | 53.31 | 58.01 | 46.14 | 55.09 | 56.17 |

$^a$Values represent the hepatoprotective activity percent mean of six animals in each group, Mice: Swiss albino (25–30 g) male. Unit: each unit is $\mu$ mole pyruvate/min/L.
$^b$is $\mu$ mole of p-nitrophenol formed/min/ L,
$^c$is n moles MDA/g liver.,
$^d$is $\mu$ mole GSH/g liver

EXAMPLE 2

Treatment of experimental animals with the A001 using paracetamol as hepatotoxins, reduced the elevated levels of serum GPT, GOT, ALP, bilirubin, TG and hepatic lipid peroxidation and increased the GSH levels. It was more effective than silymarin in reducing the elevated levels of by paracetamol (Table 1 as given above). The hepatoprotective activity observed with A001 was serum: GPT-84.02%; GOT-85.08%; ALP-91.33%; and in liver homogenate: LP-89.10% & GSH-95.11%. It was also effective against the galactosamine and with $CCl_4$ induced damage and the hepatoprotection observed with A001 was serum: GPT-73.18%; GOT-66.76%; ALP -71.27%; Bilirubin-66.07%; TG-62.68%; and in liver homogenate: LP-71.99%; & GSH -64.61%, (Table-2 as given below) and with $CCl_4$ 87.66%, 90.15%, 92.16%, 89.66%, 97.69% and 86.92% & 98.16% respectively and same with silymarin (Table-3 as given below).

30.67%; ALP-34.58%; Bilirubin-33.92%; TG-41.83%; and in liver homogenate: LP-33.43%; & GSH-27.35%, Table-2 (as given below example 2).

EXAMPLE 4

Treatment of experimental animals with the F002 using paracetamol as hepatotoxins, reduced the elevated levels of serum GPT, GOT, ALP, bilirubin, TG and hepatic lipid peroxidation and increased the GSH levels. It was more effective than silymarin in reducing the elevated levels of by paracetamol (Table 1 as given below example 1). The hepatoprotective activity observed with F002 was serum: GPT-40.99%; GOT-52.63%; ALP-35.03%; and in liver homogenate: LP-50.81% & GSH-58.42%, Table-1 (as given

TABLE 2

RJM/0024/P01/A001/F002, RJM/0024/P01/A001/F003, RJM/0024/P01/A001/F004 and silymarin (pre-treatment fed at 48 h, 24 h, 2 h before and 6 h after hepatotoxin) against the D-Galactosamine (GalN) [(300 mg/kg in normal saline, sub cutaneously (s.c.) induced hepatic injury in rats[a]
% Hepatoprotection

| Treatment | Dose Mg/kg (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid Peroxidation[c] | Glutathione[d] |
| A001 + GalN | 125 | 73.18 | 66.76 | 71.27 | 66.07 | 62.68 | 71.99 | 64.61 |
| F001 + GalN | 125 | 46.09 | 30.67 | 34.58 | 33.92 | 41.83 | 33.43 | 27.35 |
| F002 + GalN | 125 | 43.72 | 36.80 | 41.02 | 46.42 | 40.63 | 42.17 | 23.07 |
| F003 + GalN | 125 | 72.06 | 58.94 | 67.27 | 73.21 | 61.10 | 68.14 | 68.54 |
| F004 + GalN | 125 | 42.08 | 33.69 | 39.51 | 55.30 | 38.43 | 50.35 | 27.86 |
| Silymarin + GalN | 50 | 65.17 | 59.73 | 55.79 | 66.07 | 61.26 | 63.72 | 54.35 |

[a]: Values represent the hepatoprotective activity percent mean of six animals in each group, Rats: Wistar, (150–175 g) male. Unit: each unit is $\mu$ mole pyruvate/min/L.
[b]: is $\mu$ mole of ρ-nitrophenol formed/min/L,
[c]: is n moles MDA/g liver.,
[d]: is $\mu$ mole GSH/g liver

TABLE 3

Hepatoprotective activity (in vivo) of RJM/0024/P01/A001 and silymarin (pre-treatment fed at 48 h, 24 h, 2 h, before and 6 h after toxin) against $CCl_4$ (1 ml/kg, p.o.) induced hepatic injury in rats[a].
% Hepatoprotection

| Treatment | Dose Mg/kg (p.o.) | Serum parameters | | | | | Hepatic parameters | |
|---|---|---|---|---|---|---|---|---|
| | | GPT (Units) | GOT (Units) | ALP[b] | Bilirubin (mg %) | Triglycerides (mg %) | Lipid Peroxidation[c] | Glutathione[d] |
| AOOl + $CCl_4$ | 250 | 87.66 | 90.15 | 92.16 | 89.66 | 97.69 | 86.92 | 98.16 |
| Silymarin + $CCl_4$ | 50 | 54.08 | 50.07 | 46.00 | 52.08 | 46.21 | 54.03 | 56.35 |

[a]: Values represent the hepatoprotective activity percent mean of six animals in each group, Rats: Wistar, (150–175 g) male. Unit: each unit is | $\mu$ mole pyruvate/min/L.
[b]: is $\mu$ mole of ρ-nitrophenol formed/min/L,
[c]: is n moles MDA/g liver.,
[d]: is $\mu$ mole GSH/g

EXAMPLE 3

Treatment of experimental animals with the F001 using paracetamol as hepatotoxins, reduced the elevated levels of serum GPT, GOT, ALP, bilirubin, TG and hepatic lipid peroxidation and increased the GSH levels. It was more effective than silymarin in reducing the elevated levels of by paracetamol (Table 1 as given below example 1). The hepatoprotective activity observed with F001 was serum: GPT-30.40%; 48.62%; ALP-30.64%; and in liver homogenate: LP-54.35% & GSH-49.65% Table-1, which indicates very mild activity less than the (+) Ve control silymarin. With galactosamine induced damage and the hepatoprotection observed with F001 was serum: GPT-46.09%; GOT-below example 1). With galactosamine induced damage and the hepatoprotection observed with F002 was serum : GPT-43.72%; GOT-36.80%; ALP-41.02%; Bilirubin-46.42%; TG-40.63%; and in liver homogenate: LP-42.17%; & GSH-23.07%, Table-2 (as given below example 2).

EXAMPLE 5

Treatment of experimental animals with the F003 using paracetamol as hepatotoxins, reduced the elevated levels of serum GPT, GOT, ALP, bilirubin, TG and hepatic lipid peroxidation and increased the GSH levels. It was more effective than silymarin in reducing the elevated levels of by paracetamol (Table 1 as given below example 1). The hepatoprotective activity observed with F003 was serum: GPT-60.00%; GOT-61.79%; ALP-70.82%; and in liver homogenate: LP-78.72% & GSH-80.75%, Table-1 as given below example 1, which indicates the strongest activity compared with silymarin.

EXAMPLE 6

Treatment of experimental animals with the F004 using paracetamol as hepatotoxins, reduced the elevated levels of serum GPT, GOT, ALP, bilirubin, TG and hepatic lipid peroxidation and increased the GSH levels. It was more effective than silymarin in reducing the elevated levels of by $$H = \left(1 - \frac{TC - V}{VC - V}\right) \times 100$$

The results are compared and calculated as:

V=is the negative control group treated with vehicle as normal saline or liquid paraffin only.

T C=is the Drug+$CCl_4$ treated group.

V C=is the Vehicle+$CCl_4$ treated group

TABLE 4

Hepatoprotective activity (in vivo) of RJM/0024/P01/A001 against CCU induced hepatic injury in rats[a].

| Treatment | Dose mg/kg$^{-1}$ (p.o.) | Serum parameters | | | | | Liver homogenate parameters | |
|---|---|---|---|---|---|---|---|---|
| | | GPT (Units) | GOT (Units) | ALP[b] | Bilirubin (mg %) | Triglycerides (mg %) | Lipid Peroxidation[c] | Glutathione[d] |
| Vehicle only | | 102.86 ± 6.79 | 100.40 ± 8.38 | 2?.69 ± 1.59 | 0.18 ± 0.01 | 17.4 ± 1.76 | 31.80 ± 2.83 | 6.90 ± 0.51 |
| Vehicle + $CCl_4$ | | 1634.29 ± 69.24 | 1310.54*74.74 | 67.90*3.57 | 0.50 ± 0.02 | 43.81 ± 2.22 | 69.68 ± 2.70 | 2.35 ± 0.21 |
| AGO? + $CCl_4$ | 250 | 291.76 ± 27.17(87.66) | 219.49t18.64(90.15) | 30.84 ± 232 (92.16) | 0.2I5 ± 0.02 (89.66) | 18.02 ± 2.04 (97.69) | J6.75 ± 2.96 (86.92) | 6.8U0.32 (98.16) |
| silymarin + $CCl_4$ | 50 | 806.08 ± 63.89(54.08) | 704.51 ± 44.59(50.07) | 49.40 ± 1.97 (46.00) | 0.33 ± O.I6 (52.08) | 31.61 ± 1.88 (46.21) | 49.21 ± 2.96 (54.03) | 4.91 ± 0.33 (56.35) |

The test material was fed at 48 h, 24 h, 2 h before and 6 h after toxin $CCl_4$ (1 ml/kg, p.o.). Serum and liver were collected after 24 h after treatment of toxin.
[a]: Values represent the Mean + S.E. of six animals (rats, wistar, 150–175 g body weight, male) in each group. The values with in parentheses represent percent hepatoprotection. Unit: $\mu$ mole pyruvate/min./L.
[b]: $\mu$ mole of p-nitrophenol formed/min/ L,
[c]: n moles MDA/g liver..
[d]: is $\mu$ mole GSH/g Liver.

paracetamol (Table 1 as given below example 1). The hepatoprotective activity observed with F004 was serum: GPT-47.52%; GOT-50.34%; ALP-50.01%; and in liver homogenate: LP-53.37% & GSH-63.23%, Table-1 as given below example 1.

EXAMPLE 7

Treatment of experimental animals with extract A001 and fractions F001 to F004 using D-Galactosamine (GalN) as a hepatotoxic agent. (Please refer Table 2 as given below example 2)

EXAMPLE 8

Treatment of experimental animals with extract A001 and fractions F001 to F004 using carbon tetrachloride ($CCl_4$) as a hepatotoxic agent. (Please refer Tables 3 as given below example 2 and refer Table 4 as given before claims)

Liver injury produced by administration of $CCl_4$ mixed with liquid paraffin. It was administered orally (p.o.) by gastric intubation. The control animals received the equal volumes of liquid paraffin.(Rats)

Group wise results are compared and calculated as:

The first group served as normal control and received vehicles by gavage (normal saline and liquid paraffin) only.

The second group served as $CCl_4$ control and received by gavage vehicle (normal saline) and liquid paraffin (1:1).

The remaining groups were respective drug and $CCl_4$ by gavage.

The percentage hepatoprotective activity (H) was calculated by the following equation:

What is claimed is:

1. A method of treating subjects for developing hepatoprotection in the subjects comprising administering to the subject a pharmaceutically effective dosage of a composition comprised of extract A001 and/or fraction F003 from plant *Cryptolepis buchanani* and a pharmaceutically acceptable carrier therefore.

2. The method of claim 1, wherein the composition contains an additive selected from the group of nutrients consisting of proteins, carbohydrates, sugar, talc, magnesium stearate, cellulose, calcium carbonate and starch-gelatin paste.

3. The method of claim 1, wherein said composition is effective against hepatotoxins selected from the group consisting of Paracetamol, D-Galactosamine, and Carbon tetrachloride.

4. The method of claim 1, wherein said composition is administered orally, inhaled, or implanted.

5. The method of claim 1, wherein the composition is in the form of a capsule, tablet, syrup, concentrate, powder, granule, aerosol, or beads.

6. The method of claim 1, wherein said extract and fraction in said composition are in a ratio ranging between 1:10 to 10:1.

7. The method of claim 1, wherein the composition is administered at concentration ranging between 100–500-mg/kg.

8. The method of claim 1, wherein the composition is administered at concentration about 270 mg/kg.

9. The method of claim 1, wherein said composition shows % hepatoprotective activity of (a) GPT ranging between 70–90, (b) GOT ranging between 65–95, (c) ALP ranging between 70–95, (d) Bilirubin ranging between 65–95, (e) Triglycerides ranging between 60–99, (f) Lipid Peroxidation ranging between 70–95, and (g) Glutathione ranging between 65–99.

10. The method of claim 1, wherein said composition shows % hepatoprotective activity of (a) GPT ranging between 60–80, (b) GOT ranging between 55–65, (c) ALP ranging between 65–75, (d) Bilirubin ranging between 70–80

(e) Triglycerides ranging between 60–65, (f) Lipid Peroxidation ranging between 65–85, and (g) Glutathione ranging between 65–85.

11. The method of claim 1, wherein the subjects are animals and/or human beings.

12. The method of claim 1, wherein said method shows said composition to be more effective than commercially available hepatoprotectants.

13. The method of claim 1, wherein said method using said composition has no adverse effect on health.

* * * * *

UNITED STATES PATENT AND TRADEMARK OFFICE
CERTIFICATE OF CORRECTION

PATENT NO. : 6,686,375 B2
DATED : February 3, 2004
INVENTOR(S) : Ghulam Nabi Qazi et al.

It is certified that error appears in the above-identified patent and that said Letters Patent is hereby corrected as shown below:

<u>Title page,</u>
Item [75], Inventors, "Krishnan Avtar SURI" should read -- Krishan Avtar SURI --; ninth inventor's name, "Bal Krishnan KAPAHI" should read -- Bal Krishan KAPAHI --.

Signed and Sealed this

Twenty-second Day of June, 2004

JON W. DUDAS
*Acting Director of the United States Patent and Trademark Office*